United States Patent [19]

Taniyama et al.

[11] Patent Number: 4,711,842
[45] Date of Patent: Dec. 8, 1987

[54] METHOD FOR PRODUCTION OF BIOLOGICALLY ACTIVE SUBSTANCES

[75] Inventors: Tadayoshi Taniyama, Tokyo; Koichi Yoshida, Shizuoka, both of Japan

[73] Assignee: Asahi Kasei Kogyo Kabushiki Kaisha, Osaka, Japan

[21] Appl. No.: 589,832

[22] Filed: Mar. 15, 1984

[30] Foreign Application Priority Data

Mar. 15, 1983 [JP] Japan .................................. 58-41409

[51] Int. Cl.$^4$ ....................... C12P 21/00; C12N 15/00
[52] U.S. Cl. .................... 435/68; 435/172.2; 435/240.26
[58] Field of Search ....................... 435/68, 172.2, 240; 935/99, 100, 101, 102

[56] References Cited

U.S. PATENT DOCUMENTS 4,438,032  3/1984  Golde et al. ........................... 424/85
4,529,694  7/1985  Lazarus .................................. 424/85
4,544,632  10/1955  Yamamura et al. ................... 435/68

FOREIGN PATENT DOCUMENTS 0044722  1/1982  European Pat. Off. .

OTHER PUBLICATIONS

Miyamura et al., J. Antibiotics, vol. 36, No. 6, 1983, pp. 684–687.
Smith et al., J. Chem. Soc., Perkins Trans. I, vol. 22, p. 2811, 1972.
Bloom et al., Ed., "In Vitro Methods in Cell-Modulated Immunity", p. 353.
Matthew, Immunology, vol. 44, pp. 135–142, 1981.

*Primary Examiner*—Blondel Hazel
*Attorney, Agent, or Firm*—Sughrue, Mion, Zinn, Macpeak, and Seas

[57] ABSTRACT

A method of producing biologically active substances using a hybrid cell line obtained by fusing (1) a human tumor cell line which does not grow in a medium containing aminopterin or/and azaserine or cell line derived therefrom with (2) a human non-tumor macrophage. The human tumor macrophage cell line may be either a thymidine kinase-deficient cell line of U-937 or a thymidine kinase-deficient cell line of THP-1, the non-tumor macrophage may be alveolar macrophage, splenic macrophage, peripheral blood monocyte, peritoneal macrophage, hepatic macrophage, placental macrophage, or thymic macrophage, and the biologically active substance produced is a tumoricidal substance or interleukin-1.

5 Claims, No Drawings

METHOD FOR PRODUCTION OF BIOLOGICALLY ACTIVE SUBSTANCES

FIELD OF THE INVENTION

The present invention relates to a method of producing a biologically active substance which comprises fusing human macrophages capable of elaborating a medicinally useful, biologically active substance with a human tumor macrophage cell line or a cell line derived therefrom to produce a hybrid cell line capable of proliferation, and employing this hybrid cell line so established for production of the biologically active substance.

BACKGROUND OF THE INVENTION

Several reports exist on attempts to produce medicinally useful, biologically active substances by means of human macrophages. However, at the present time, the only promising route of harvesting such a biologically active substance in a practically useful quantity is by way of a cell line established from a tumor-bearing patient. Examples of human tumor macrophage cell lines established from a tumor-bearing patient include U-937 (*International Journal of Cancer*, 17, 565–577 (1976)), THP-1 (*International Journal of Cancer*, 26, 171–176 (1980)), J-111 (*Blood*, 10, 1010 (1955)), HL-60 (*Nature*, 270, 347 (1977)), KG-1 (*Science*, 200, 1153 (1978)) and K-562 (*Blood*, 45, 321–334 (1975)).

Referring to reports on attempts to obtain biologically active substances from these cell lines, the methods proposed by S. B. Mizel et al, *Interleukins, Lymphokines, and Cytokines*, Academic Press, Inc. 401–407 (1983) and T. Krakauer et al, *Cellular Immunology*, 80, 223–229 (1983) may be mentioned for the production of interleukin-1 from THP-1; R. Palacios et al, *European Journal of Immunology*, 12, 895–899 (1982) may be mentioned for the production of interleukin-1 from U-937; and R. H. Butler et al, *Cellular Immunology*, 78, 368–374 (1983) may be mentioned for the production of interleukin-1 from CM-S. E. V. Gaffney et al, *Cancer Research*, 43, 3668–3673 (1983), for instance, describes a method using THP-1 for the production of tumoricidal factors.

Human macrophage cell lines established from tumor-bearing patients may be stimulated by lipopolysaccharide, plant lectin or lymphocyte secretions to induce the secretion of a variety of biologically active substances as described in *Proc. Natl. Acad. Sci. USA*, 79, 5379–5383 (1982). However, since the output of such substances is very small and the kinds of cell lines are virtually limited to those mentioned above, the techniques are of little practical use.

Several methods for enabling human macrophages to proliferate may be contemplated, such as the method in which cells are tumorized with a virus or chemical carcinogen, the method which comprises picking up the desired cells from among serially passaged cells, and the method utilizing fusion with tumor cells, for instance. Of these and other methods, the cell fusion technique is the most suitable in that, once established, the technique is applicable to a large variety of cells and the problem of carcionogenic chemical residues can be obviated.

As regards past studies on the fusion of macrophages, it has been reported, for example, in A. H. Warfel, *Experimental and Molecular Pathology*, 28, 163–176 (1978) and S. Sone et al, *Americal Journal of Pathology*, 103, No. 2, 234–246 (1981), that giant cells are formed by fusion of homologous cells of some aminals such as mice, rats and rabbits. Regarding fusion between heterologous cells, the only report available describes that fusion between rat and mouse macrophages (P. Stahl et al, *The Journal of Cell Biology*, 93, 49–56 (1982)) and no report is known on a successful fusion between human macrophages.

SUMMARY OF THE INVENTION

The possibility of fusing a human macrophage-derived tumor cell line with a human non-tumor macrophage cell has now been investigated and a fusion technique has now been successfully established by improving the conventional procedure using polyethylene glycol as a fusing agent. As a result, a method for producing desired biologically active substance or substances has been established.

This invention relates to a method for producing a pharmaceutically useful biologically active substance in a practically useful quantity. The method of this invention comprises effecting cell fusion between a human non-tumor macrophage capable of producing a pharmaceutically useful biologically active substance and a human tumor macrophage cell line incapable of growing in a medium containing aminopterin or/and azaserine or a cell line derived therefrom to prepare a hybrid cell capable of proliferation and, then, using the hybrid cell line for production of the pharmaceutically useful biologically active substance.

The human tumor macrophage cell line which can be used includes desirably a thymidine kinase-deficient cell line of U-937 or a thymidine kinase-deficient cell line of THP-1 in terms of stability of the cell line as well as in the ease of cell fusion procedure. The human non-tumor macrophage can be macrophages of various organs, peripheral blood monocytes, etc.

By improving the conventional cell fusion technique using polyethylene glycol, it has not been found that the efficiency of fusion can be increased and, accordingly, a fusion between human macrophage cells which had never been possible by the prior art technology can now is accomplished, thereby enabling one to produce a human-derived pharmaceutically useful biologically active substance in practically useful quantities. In accordance with this invention, it is now possible to eliminate the problem of antigenicity which can arise if a substance of non-human origin is administered to human, with the result that the invention provides a very useful means for obtaining therapeutically active materials of value for the treatment of cancer, immune diseases, thrombosis, etc.

DETAILED DESCRIPTION OF THE INVENTION

In greater detail, the present invention provides a method of producing a biologically active substance using a hybrid cell obtained by fusing a human tumor macrophage cell line with a human non-tumor macrophage.

Any known cell lines such as U-937, THP-1, J-111, HL-60 and K-562 can be employed as the human tumor macrophage cell line. These human tumor macrophage cell lines are available from the authors of the aforesaid literatures. Further, U-937 has been deposited at The American Type Culture Collection (Accepted No. CRL-1593). However, in terms of the stability of cell lines and the ease of fusion procedure in connection with floatation, cell lines of U-937 and THP-1 are preferred. Other cell lines may also be employed for the purposes of the present invention, for hybrid cells obtainable by using different cell lines have different characteristics.

In the actual fusion of such a tumor cell line with a human non-tumor macrophage cell, the tumor cell line is previously treated so as to render it resistant to 5-bromodeoxyuridine and a cell line deficient in thymidine kinase is selected. Although the procedure involved is described in detail hereinafter, the intention is to permit a selective proliferation of the hybrid cell and harvest the same.

Alveolar macrophages, splenic macrophages, hepatic macrophages, peritoneal macrophages, placental macrophages, peripheral blood monocytes, thymic macrophages and so forth can be suitably employed as the human non-tumor macrophage cell. However, macrophage cells are widely distributed in body tissues and the above enumeration is not to be interpreted as exclusive or limiting. These human non-tumor macrophage cells can be easily obtained from various human organs in a routine manner. While such non-tumor macrophages are generally subjected as is to the cell fusion procedure, they may of course be previously stimulated with a stimulating agent as described in *Proc. Natl. Acad. Sci. USA*, 79, 5379-5383 (1982). Examples of the stimulating agent include a lipopolysaccharide (hereinafter referred to as LPS), concanavalin A, phytohemagglutinin, pokeweed mitogen, vitamin A and its derivatives, phorbol esters, muramyl dipeptide, Bacille Calmette-Guérin, proteose peptone, lentinan, pisibanil, dimethyl sulfoxide, lymphokine, etc.

Fusion is effected by mixing a human macrophage-derived tumor cell line with a human non-tumor macrophage in the presence of a fusing agent at room temperature (about 20°-40° C.). There are known various fusing agents such as polyethylene glycol solution, inactivated Sendai virus, etc., as described in for example, Taniyama et al, *J. Exp. Med.*, 156. 1286-1291 (1982) and Köhler et al, *Nature*, 256, 495 (1975) and although there is no particular limitation on the fusing agents that can be employed, a polyethylene glycol solution is easy to prepare and use. Following the fusion, the unfused non-tumor macrophages die gradually and do not interfere with the harvest of the hybrid cell line but since the unfused tumor cells do not die, some ingenuity is required for separating the tumor cells from the hybrid cells.

While the separation of the hybrid cell line from the unfused tumor cell line can be accomplished by comparing the properties of individual colonies, for example, by cloning limiting dilution in agar medium, it is more expedient to previously select an enzymatically deficient tumor cell line which will not survive in a medium containing aminopterin or/and azaserine from the tumor cell line and use such a deficient line for cell fusion.

Since an enzymatically deficient tumor cell line which dies in the presence of aminopterin is also killed by azaserine, the present procedure will be described below with reference to aminopterin only. It should be understood that the following description is equally applicable to azaserine as well.

Thus, after fusion, the hybrid cell line alone can be selectively allowed to proliferate by culturing the system in an aminopterin-containing medium. When a cell line deficient in hypoxanthineguanine-phosphoribosyl transferase (abbreviated as HGPRT) is to be established, a cell line which is capable of proliferating in a medium containing such a reagent as 8-azaguanine or 6-thioguanine is selected. To isolate a thymidine kinase-deficient cell line, a line capable of proliferating in a medium containing 5-bromodeoxyuridine is selected.

Since the necessary concentration of the reagent depends on the responsiveness thereto of the cell line used, the line is first cultured in media containing the reagent in different concentrations to determine the reagent concentration corresponding to $\frac{1}{2}$ of the proliferation rate in the absence of the reagent and, then, increasing the reagent concentration to a level equal to 20-100 times this concentration gradually over a period of 2 to 6 months. The enzymatically deficient-tumor cell line thus prepared is incapable of surviving in aminopterin-containing media. This tumor cell line is hereinafter referred to as the aminopterin-sensitive tumor cell line. In order to confirm that the tumor cell line thus obtained is truely an aminopterin-sensitive tumor cell line, it is cultured in a medium containing aminopterin at various concentrations for 15 days to confirm that the tumor cell line will die completely and the lethal concentration of aminopterin for this deficient tumor cell line is determined. It is desirable for the concentration range of aminopterin from the minimal lethal concentration required to kill all the deficient tumor cell population in 15 days to 100 times that minimal lethal concentrtion to be used as the aminopterin concentration of the screening medium to be used following the fusion.

The cell fusion technique is described below in detail.

The human non-tumor macrophages can be isolated from various human organs. Peripheral blood monocytes can be obtained by Ficoll-Conray gradient centrifugation at 400 g for 30 minutes to obtain a peripheral blood lymphocyte-rich fraction as an intermediate fraction. Peritoneal macrophage can be obtained by subjecting ascites from a patient with ascites retention to centrifugation to collect the cells. Splenic, thymic, placental or hepatic macrophages can be obtained by mincing isolated tissue, separating the solid fraction by means of a stainless steel screen, lysing the contaminant erythrocytes with a 0.14M aqueous solution of ammonium chloride, dispersing the cells in a cell culture medium, spreading the dispersion over a plastic plate precoated with fetal calf serum, and after a few hours, detaching the adherent cells from the plastic plate with trypsin or ethylenediamine tetraacetate. For alveolar macrophages, alveolar washes from bronchopulmonary lavage are used as such.

A suspension containing human non-tumor macrophages obtained as described above is then mixed with aminopterin-sensitive tumor cell line and the protein components inclusive of fetal calf serum are completely removed by centrifugation. The mixing ratio (cell count) of the two kinds of cells, is not limited, and may range from about 100:1 to about 1:100.

Then, the cell mixture is preincubated in a serum-free medium containing 1 to 1,000 μg/ml of a phytoagglutinin such as Con A, phytohemagglutinin, pokeweed mitogen or like, collagen or fibronectin in a 5% $CO_2$ atmosphere at 37° C. for 5 to 60 minutes. It was found that with this pretreatment the efficiency of fusion of macrophages is remarkably increased. Of course, the respective cells may be independently pretreated in a like manner prior to mixing. While not desiring to be bound, the above result arises because the pretreatment appears to cause an aggregation of cells thereby improving the efficiency of intercellular contact and, hence, improving the efficiency of fusion.

Then, polyethylene glycol having a molecular weight of about 1,500 to about 6,000 as a fusion accelerator is dissolved in protein-free medium or balanced salt solution in a concentration of 35 to 55%, and the solution is added slowly dropwise in a proportion of 0.1 to 1 ml per $10^7$ total cells. The system is allowed to stand for 2 to 3 minutes, followed by washing with protein-free media to sufficiently dilute the polyethylene glycol. The medium containing the cells is then dispersed in a medium containing aminopterin in a concentration from the minimal lethal concentration leading to a complete death of all the aminopterin-sensitive tumor cell population to 100 times the minimal lethal concentration, as well as hypoxanthine and thymidine which are fused cell proliferation accelerators (hereinafter abbreviated as HAT medium) and the dispersion is distributed in a 96-well microtest plate. The plate is placed in a carbon dioxide incubator for proliferation of fused cells. While the concentrations of hypoxathine and thymidine are not limited within the range where no cytotoxic effect is produced, they are preferably used in the proportions of about $10^{-4}M$ and about $1.5 \times 10^{-5}M$, respectively.

The cells proliferating in the HAT medium are separated to confirm that they are fused cells. There may be cases in which the thymidine kinase-deficient tumor cells undergo mutation in HAT medium to revert to thymidine kinase-containing cells which multiply in the HAT medium. The above confirmation assists in discovering such occurences.

Confirmation of cell fusion is carried out by investigating the increase of the number of chromosomes which can be determined by conventional techniques, as described in, for example, M. Seabright et al, *The Lancet*, 971–972 (1971). Generally, the number of chromosomes of non-tumor human macrophages is 46, that is the number of chromosomes, of normal human diploids. The number of chromosomes of human tumor macrophages is also 46. The fused cell, of course, has a number of chromosomes in excess of 46. However, as division and proliferation is repeated some of the chromosomes may be lost and, therefore, it cannot be said that cells having less than 92 of chromosomes are not fused cells. Generally, fused cells have a distribution as to the number of chromosomes.

For determination of the number of chromosomes, about $10^6$ cells are treated in a routine medium containing $10^{-7}M$ of colcemid for 30 to 60 minutes, treated further with a hypotonic salt solution, fixed with acetic acid-methanol (1:3, v/v), dripped onto a cooled slide glass plate, dried, stained with Giemsa, and examined under a optical microscope.

To detect the biologically active substance elaborated by the fused cells, these cells were cultured in a medium containing a stimulating agent such as LPS, concanavalin A, phytohemagglutinin, pokeweed mitogen, vitamin A and its derivatives, phorbol ester, muramyl dipeptide, Bacille Calmette-Guérin, proteose peptone, lentinan, pisibanil, dimethyl sulfoxide or lymphokine, and the supernatant of the culture was used as a material. While a single fused cell elaborates various biologically active substances, the product pattern appears to be altered by different stimulation methods. It is also possible, by cloning techniques, to secure a single kind of biologically active substance in an increased yield.

Tumoricidal substance was determined by a cytotoxicity assay using mouse leukemia cells, while interleukin-1 was assayed by the rate of uptake of tritium-labeled thymidine by mouse thymocytes (determination of promoting effect on DNA synthesis).

The production of biologically active substance by the fused cell line

1. As regards the tumoricidal substance, all fused cells derived from different parent strains produced, on stimulation, a substance displaying an injurious effect on mouse L cells in culture and the activity of the substance was markedly higher than that of the parent human tumor macrophage cell line and either equivalent to, or higher than, that of the other parent human non-tumor macrophage. Moreover, these fused cells were capable of proliferation.

2. As for interleukin-1, as in the case of the tumoricidal substance, the fused cells had an activity higher than that of human tumor macrophage cell lines and either equal to, or even higher than that of human non-tumor macrophages, and were capable of proliferation.

Thus, the fused cell line according to the present invention was confirmed to produce a tumoricidal substance and interleukin-1 in large quantities. The fact that this fused cell is a hybrid cell between human cells and proliferates indicates that it can be utilized for producing these substance of human origin in large quantities.

The establishment of this fused cell line solves all the problems in the prior art so far considered difficult to solve, i.e., the difficulty in obtaining a substance which is a promising agent for the treatment of cancer and various immune diseases but could not be procured in a useful quantity, and the difficulty in eliminating the problem of antigenicity which tends to occur when a non-human derived substance is administered to humans. Therefore, the present invention has a considerable significance in the maintenance of health and welfare of mankind.

The following examples are given to further illustrate the present invention, but are by no means to be construed as limiting the present invention. Unless otherwise indicated, all parts, percents, ratios and the like are by weight.

EXAMPLE 1

Human peripheral blood (50 ml) was distributed in 5-ml portions into centrifuge tubes each containing 3 ml of a Ficoll-Conray solution to form a layer upon the Ficoll-Conray solution, followed by centrifugation at 400 g for 30 minutes. A fraction obtained in the form of an intermediate layer (peripheral blood lymphocyte fraction) was collected and suspended in 20 ml of 10% fetal calf serum-containing RPMI-1640 medium. The suspension was spread on two plastic petri dishes 100 mm in diameter and incubated in a carbon dioxide incubator (5% $CO_2$) at 37° C. overnight. The plastic dishes used were those prepared by placing about 2 ml of fetal calf serum therein, allowing them to stand in a refrigerator for at least 8 hours and then removing the fetal calf serum. The cells adhering to the surface of the ,lastic dishes were collected by adding 2 ml of PBS solution containing 0.025% of trypsin and 0.005% of EDTA, allowing the whole to stand at room temperature for 3 minutes and collecting the cells adhered to the surface with a rubber policeman. The resultant cells (count: $1.5 \times 10^7$) were for the most part monocytes and their survival rate as determined by the trypan blue exclusion test was more than 95%.

The thymidine kinase-deficient line (U-937 (TK$^-$)) of U-937 which is a human tumor macrophage cell line ($3 \times 10^7$ cells) and produced as described hereinafter in Reference Example 1 was mixed with the monocytes obtained as described above and the mixture suspended in RPMI-1640. The cells were washed by centrifugation to remove the protein component. This procedure was repeated twice, after which the cells were suspended in 3 ml of RPMI-1640, followed by addition of 0.1 mg of human fibronectin. The mixture was allowed to stand in a carbon dioxide incubator for 30 minutes. Using RPMI-1640, the cells were washed by centrifugation, and a 40% solution of polyethylene glycol (mol. wt. 2,000) in Hank's solution was added to the cell pellet. The cells were then dispersed in 60 ml of HAT medium, spread on three 96-well plates and incubated in a carbon dioxide incubator at 5% $CO_2$ and 37° C.

After 25 days, wells showing proliferation of cells were noted. These cells were confirmed to be fused cells by examination of the number of chromosomes. This examination of the number of chromosomes was carried out by the procedure described hereinafter. The results obtained are shown in Table 1 below.

TABLE 1

| Method of fusion | Number of wells showing proliferation of cells (among 96 × 3 = 288 wells) | % of cells having 50 or more chromosomes |
|---|---|---|
| Treatment with fibronectin | 15 | 35–68 |

EXAMPLE 2

The production of a tumoricidal substance by the fused cell line obtained as described in Example 1 was investigated. The fused cells and, as controls, the parent U-937 (TK$^-$) and pripheral blood monocytes ($10^6$ cells each) were respectively suspended in 1 ml of RPMI-1640 medium containing 7.5% of fetal calf serum in 24-well plastic dishes, followed by addition of 10 μg/ml of LPS. The cells were incubated at 5% $CO_2$ and 37° C., and 20 hours after the addition of LPS, the supernatants were pooled and the cytotoxic effect against mouse leukemia cells was investigated.

To determine the cytotoxic effect on mouse L cells, the culture supernatant was distributed in 100 μl portions into the wells of 96-well plastic plates, either as it was or after 2, 4, 8, 16, 32, 64 and 128-fold dilutions with MEM containing 1% of fetal calf serum. Then, $10^5$ mouse L cells were diluted with 1 ml of MEM containing 1% of fetal calf serum and 100 μl of the suspension was added to each dish and incubated in a 5% $CO_2$ atmosphere at 37° C. for 2 days. Then, 20 μl of 25% glutaraldehyde was added, followed by standing at room temperature for 15 minutes. After fixation, the cells were washed with water 4 times and dried at 50° C. for 10 minutes. Then, 100 μl of a 0.2% solution of crystal violet in 2% ethanol was added and the mixture was allowed to stand at room temperature for 15 minutes. The cells were then washed with water 4 times and dried at 50° C. for 10 minutes. Thereafter, 200 μl of a 1:1 (v/v) mixture of 0.1M $Na_2HPO_4$ and ethanol was added and, after swirling at room temperature for 3 minutes, the absorbance at 610 nm was measured. The results obtained are shown in Table 2 below. In the table, A-1, A-2 and A-3 represent the colonies of fused cells obtained using peripheral blood monocytes and U-937 (TK$^-$).

TABLE 2

| Cell line | Dilution factor for culture supernatant at a 50% kill of mouse L cells |
|---|---|
| Fused cell line A-1 | 10 |
| Fused cell line A-2 | 4 |
| Fused cell line A-3 | 8 |
| U-937 (TK$^-$) | <2 |
| Peripheral blood monocytes | 2 |

EXAMPLE 3

Using the thymidine kinase-deficient cell line of THP-1 (abbreviated as THP-1 (TK$^-$)) produced as described hereinafter in Reference Example 2 as a human tumor macrophage cell line, the procedure as described in Example 1 was followed to effect a fusion with peripheral blood monocytes (obtained as described in Example 1). As a result, fused cells were obtained in 10 of the 288 wells. The production of a tumoricidal substance by this fused cell line was investigated using the same procedure as described in Example 2. The results obtained are shown in Table 3 below. In the table, B-1 and B-2 represent the colonies of fused cells obtained using peripheral blood monocyte and THP-1 (TK$^-$).

TABLE 3

| Cell line | Dilution factor for culture supernatant at a 50% kill of mouse L cells |
|---|---|
| Fused cell line B-1 | 8 |
| Fused cell line B-2 | 4 |
| THP-1 (TK$^-$) | <2 |
| Peripheral blood monocyte | 2 |

EXAMPLE 4

Cells were collected from 50 ml of washings from the washing of human lungs by centrifugation to obtain $1.0 \times 10^7$ alveolar macrophages. The cell survival rate was 93% as determined by trypan blue exclusion test.

$1.0 \times 10^7$ human alveolar macrophages were mixed with $3 \times 10^7$ U-937 (TK$^-$) cells produced as described in Reference Example 1 and the mixture was suspended in RPMI-1640. The cells were washed by centrifugation to remove the protein component. Then, cell fusion was effected using the same procedure as described in Example 1. Fused cells were obtained in 3 of 250 wells. Of these fused cells, 30 to 42% had 50 or more chromosomes.

500 ml of ascites from a patient with cancerous peritonitis were centrifuged to collect cells and after the erythrocytes were lyzed with 0.14M ammonium chloride, the cells were suspended in 20 ml of RPMI-1640 medium containing 10% of fetal calf serum. Thereafter, the procedure as described in Example 1 was followed to obtain $8 \times 10^6$ peritoneal macrophages adhering to plastic dish surfaces. The cells were mixed with $2 \times 10^7$ U-937 (TK$^-$) cells and the fusion was carried out in the same manner as Example 1, whereby fused cells were obtained in 5 of 200 wells. Of these fused cells, 38 to 55% had 50 or more chromosomes.

The fused cell line between U-937 (TK$^-$) and alveolar macrophage and the fused cell line between U-937

(TK$^-$) and peritoneal macrophage were stimulated with LPS in the same manner as described in Example 2 and the supernatants were assayed for interleukin-1 activity. At the same time, the fused cell line A-1 obtained using peripheral blood monocyte and U-937 (TK$^-$) according to Example 2 was also similarly stimulted with LPS and the supernatant was assayed for interleukin-1 activity.

The assay of interleukin-1 activity was based on the uptake of tritium-labeled thymidine by mouse thymocytes. Thus, $10^6$ fused cells were cultured in 1 ml of serum-free RPMI-1640 medium containing 10 μg of LPS in a carbon dioxide incubator for 24 hours. The culture supernatant was pooled and added to 1 ml of 5% human serum-MEM medium containing $5 \times 10^6$ thymocytes from a C3H/HeJ mouse aged 6 weeks, and incubated in a carbon dioxide incubator. After 48 hours, thymidine labeled with 1 μCi of tritium was added and the incubation was continued. After 72 hours, the radioactivity of the culture supernatant was determined. The above procedure was carried out in two runs, i.e., in the absence of concanavalin A in MEM medium and in the presence of 3 μg/ml of concanavalin A. The assay of interleukin-1 activity was also carried out for human peripheral blood monocyte, alveolar macrophage, peritoneal macrophage and U-937 (TK$^-$) using the same procedure. The results obtained are shown in Table 4 below.

TABLE 4

| Cell Line | | Uptake of tritium-labeled thymidine | |
|---|---|---|---|
| | | −Concanavalin A | +Concanavalin A |
| | | (cpm/5 × $10^6$ thymocytes) | |
| Peritoneal macrophage | −LPS | 500 | 48,000 |
| | +LPS | 14,000 | 145,000 |
| Peripheral blood monocyte | −LPS | 400 | 40,000 |
| | +LPS | 17,000 | 125,000 |
| Alveolar macrophage | −LPS | 600 | 63,000 |
| | +LPS | 25,000 | 200,000 |
| U-937 | −LPS | 400 | 13,000 |
| | +LPS | 10,000 | 52,000 |
| U-937 (TK$^-$)/peritoneal macrophage fused cell | −LPS | 600 | 55,000 |
| | +LPS | 21,000 | 220,000 |
| Fused Cell A-1 | −LPS | 500 | 58,000 |
| | +LPS | 19,000 | 240,000 |
| U-937 (TK$^-$)/alveolar macrophage fused cell | −LPS | 600 | 78,000 |
| | +LPS | 32,000 | 350,000 |
| Control medium | −LPS | 300 | 10,000 |
| | +LPS | 1,200 | 23,000 |

EXAMPLE 5

The liver, spleen, thymus and placenta obtained postoperatively from various patients (5 gram each) were each washed with Hank's solution, miced finely with scissors, filtered through a stainless steel screen, and centrifuged to harvest the cells. The cells were lysed with 0.14M ammonium chloride and, then, wshed repeatedly by centrifugation using RPMI-1640. The pooled cells were spread on plastic plates precoated with fetal calf serum. After 3 hours, PBS solution contianing 0.025% of trypsin and 0.005% of EDTA was added to the cells adhering to the plates. The plates were allowed to stand at room temperature for 3 minutes, after which the adherent cells were detached with a rubber policeman and collected. Then, $1 \times 10^7$ cells from each cell line were mixed with $3 \times 10^7$ U-937 (TK$^-$) cells produced as described hereinafter in Reference Example 1. After pretreatment with 0.1 mg of human collagen in lieu of fibronectin used in the procedure described in Example 1, the procedure as described in Example 1 was followed to effect fusion.

Each of the fused cell lines thus obtained was assayed for cytotoxic effect against mouse L cells using the same technique as described in Example 2, and for interleukin-1 activity using the same technique as describd in Example 4. The results obtained are shown in Table 5 below.

TABLE 5

| Cell line | Dilution factor at a 50% kill of L cells | Uptake of tritium-labeled thymidine +concanavalin A (cpm/5 × $10^6$ thymocytes) | |
|---|---|---|---|
| Splenic macrophage/ U-937 (TK$^-$) fused cell | 7 | −LPS | 48,000 |
| | | +LPS | 176,000 |
| Thymic macrophage/ U-937 (TK$^-$) fused cell | 5 | −LPS | 60,000 |
| | | +LPS | 165,000 |
| Placental macrophage/ U-937 (TK$^-$) fused cell | 8 | −LPS | 61,000 |
| | | +LPS | 184,000 |
| Hepatic macrophage/ U-937 (TK$^-$) fused cell | 6 | −LPS | 68,000 |
| | | +LPS | 176,000 |
| Splenic macrophage | 5 | −LPS | 38,000 |
| | | +LPS | 124,000 |
| Thymic macrophage | 3 | −LPS | 56,000 |
| | | +LPS | 172,000 |
| Placental macrophage | 8 | −LPS | 32,000 |
| | | +LPS | 120,000 |
| Hepatic macrophage | 5 | −LPS | 65,000 |
| | | +LPS | 165,000 |
| U-937 (TK$^-$) | <2 | −LPS | 11,000 |
| | | +LPS | 48,000 |

REFERENCE EXAMPLE 1

In 50 ml of RPMI-1640 medium containing 20% of fetal calf serum was suspended $10^7$ U-937 cells, and 50 ml of a solution containing 400 μg of ethyl methanesulfonate in 1 ml of RPMI-1640 was added. The cells were incubated at 37° C. and 5% $CO_2$ for 3 hours. Subsequently, the culture was centrifuged to collect the cells, which were then washed twice with 100 ml portions of RPMI-1640. After washing, the cells were suspended in 100 ml of RPMI-1640 medium containing 10% of fetal calf serum and the suspension was distributed into four Falcon 24-well plates and incubated in a $CO_2$ incubator for 5 days. After 5 days, the medium was changed to RPMI-1640 medium containing 10% of fetal calf serum and 1 μg/ml of 5-bromodeoxyuridine and the incubation was continued in the carbon dioxide incubator. Change of the medium was thereafter conducted at 1-week intervals, with the concentration of 5-bromodeoxyuridine in the fresh media being increased stepwise from 2, 4, 8, 12, 16, 20, 24, 28 to 30 μg per ml of RPMI-1640 medium containing 10% of fetal calf serum. Cells surviving in the 10% fetal calf serum-containing RPMI-1640 medium containing 30 μg/ml of 5-bromodeoxyuridine were found in 10 wells. These cells were cultured in 10% fetal calf serum-containing RPMI-1640 medium containing $10^{-4}$M/l of hypoxanthine, $10^{-8}$M/l of aminopterin and $1.6 \times 10^{-5}$M/l of thymidine. As a result, two cell lines which died completely within 15 days were obtained. These lines were used as thymidine kinase-deficient cell lines of U-937. The thymidine kinase-deficient cell line, designated U-937(TK$^-$), has been deposited at the American Type Culture Collection in Rockville, Maryland and has accession number CRL 8849.

REFERENCE EXAMPLE 2

In 50 ml of RPMI-1640 medium containing 20% fetal calf serum was suspended $10^7$ THP-1 cells and the suspension was mixed with 50 ml of a solution containing 400 µg of ethyl methanesulfonate per ml of RPMI-1640. The mixture was incubated in a 5% $CO_2$ atmosphere at 37° C. for 3 hours. At the end of this time, the mixture was centrifuged to collect cells. Washing was carried out twice with 100 ml portions of RPMI-1640. The washed cells were suspended in 100 ml of RPMI-1640 medium containing 10% fetal calf serum and distributed into four Falcon 24-well plates, and the incubation was carried out in a carbon dioxide incubator for 5 days. After 5 days of culturing, the medium was changed to 10% fetal calf serum-containing RPMI-1640 medium containing 1 µg/ml of 5-bromodeoxyuridine and the incubation was continued in the $CO_2$ incubator. After 1 week, the concentration of 5-bromodeoxyuridine was increased to 2 µg/ml, and thereafter at 1-week intervals, the medium was sequentially changed to 10% fetal calf serum-containing RPMI-1640 medium containing a stepwise increasing concentration, i.e., 4, 8, 12, 16, 20, 25, and 30 µg/ml, of 5-bromodeoxyuridine. Finally, cells surviving in the 10% fetal calf serum-containing RPMI-1640 medium contianing 30 µg/ml of 5-bromodeoxyuridine were found in 13 wells. Then, these cells were cultured in 10% fetal calf serum-containing RPMI-1640 medium containing $10^{-4}$M/l of hypoxanthine, $10^{-8}$M/l of aminopterin and $1.6\times10^{-5}$M/l of thymidine. These cell lines which would die completely within 15 days were obtained. These lines were used as thymidine kinase-deficient cell lines of THP-1. The thymidine kinase-deficient cell line, designated THP-1(TK$^-$), has been deposited at the American Type Culture Collection in Rockville, Maryland and has accession number CRL 8850.

While the invention has been described in detail and with reference to specific embodiments thereof, it will be apparent to one skilled in the art that various changes and modifications can be made therein without departing from the spirit and scope thereof.

What is claimed is:

1. A method of producing a biologically active substance produced by a macrophage which comprises culturing a hybrid cell line obtained by fusing (1) a human tumor cell line derived from THP-1 or U-937 and which does not grow in a medium containing aminopterin, azaserine, or aminopterin and azaserine or a cell line derived therefrom with (2) a human non-tumor macrophage capable of producing said biologically active substance.

2. The method of producing a biologically active substance as set forth in claim 1, wherein said human non-tumor macrophage is selected from the group consisting of alveolar macrophage, splenic macrophage, peripheral blood monocyte, peritoneal macrophage, hepatic macrophage, placental macrophage and thymic macrophage.

3. The method of producing a biologically active substance as set forth in claim 1, wherein said hybrid cell line is cultured in a medium containing a stimulating agent.

4. The method of producing a biologically active substance as set forth in claim 3, wherein said stimulating agent is selected from the group consisting of a lipopolysaccharide, concanavalin A, phytohemagglutinin, pokeweed mitogen, vitamin A and its derivatives, phorbol esters, muramyl dipeptide, Bacille Calmette, Guérin, proteose peptone, lentinan, pisibanil, dimethyl sulfoxide and lymphokine.

5. The method of producing a biologically active substance as set forth in claim 1, wherein said human tumor cell line or said human non-tumor macrophage is treated with a substance capable of enhancing intercellular contact prior to cell fusion.

* * * * *